United States Patent
Wilson (10) Patent No.: US 9,820,694 B2
(45) Date of Patent: Nov. 21, 2017

(54) DEVICES FOR DIAGNOSING SLEEP APNEA OR OTHER CONDITIONS AND RELATED SYSTEMS AND METHODS

(71) Applicant: Louis J. Wilson, Wichita Falls, TX (US)

(72) Inventor: Louis J. Wilson, Wichita Falls, TX (US)

(*) Notice: Subject to any disclaimer, the term of this patent is extended or adjusted under 35 U.S.C. 154(b) by 88 days.

(21) Appl. No.: 14/822,850

(22) Filed: Aug. 10, 2015

(65) Prior Publication Data
US 2016/0038084 A1 Feb. 11, 2016

Related U.S. Application Data

(63) Continuation of application No. 14/336,185, filed on Jul. 21, 2014, now abandoned, which is a (Continued)

(51) Int. Cl.
*A61B 5/087* (2006.01)
*A61B 5/08* (2006.01)
(Continued)

(52) U.S. Cl.
CPC .......... *A61B 5/687* (2013.01); *A61B 5/08* (2013.01); *A61B 5/0803* (2013.01); *A61B 5/087* (2013.01); *A61B 5/0826* (2013.01); *A61B 5/091* (2013.01); *A61B 5/4818* (2013.01); *A61B 5/6852* (2013.01); *A61B 5/7275* (2013.01); *A61B 5/7278* (2013.01); *A61B 7/003* (2013.01);
(Continued)

(58) Field of Classification Search
CPC ....... A61B 5/00; A61B 5/0051; A61B 5/0048; A61B 5/0095; A61B 5/08; A61B 5/0826; A61B 5/4818; A61B 5/6847; A61B 5/6852; A61B 8/00; A61B 8/12; A61B 7/00; A61B 7/003
USPC .......................................... 600/529–543, 484
See application file for complete search history.

(56) References Cited

U.S. PATENT DOCUMENTS 3,951,136 A   4/1976   Wall
4,649,915 A   3/1987   Heyden
(Continued)

OTHER PUBLICATIONS

Notification of Transmittal of the International Search Report and the Written Opinion of the International Searching Authority, or the Declaration dated Feb. 16, 2012 in connection with International Patent Application No. PCT/US11/58395.

*Primary Examiner* — Navin Natnithithadha (57) ABSTRACT

A system includes a sensor device having a body configured to be inserted into an airway of a patient and one or more sensors mounted in or on the body. The one or more sensors are configured to collect sensor data associated with the airway of the patient. The system also includes a signal analyzer configured to analyze the sensor data. The one or more sensors could include one or more microphones. The signal analyzer could identify volume and/or pitch characteristics of the sensor data, perform pattern recognition to identify one or more patterns using the volume and/or pitch characteristics, and use the one or more patterns to identify a type, a location, and/or a degree of airway obstruction. This could be done, for instance, to determine if the patient suffers from obstructive sleep apnea or other condition that affects his or her airway.

21 Claims, 5 Drawing Sheets

Related U.S. Application Data continuation of application No. 13/167,165, filed on Jun. 23, 2011, now Pat. No. 8,784,329.

(60) Provisional application No. 61/413,736, filed on Nov. 15, 2010.

(51) Int. Cl.
    *A61M 16/04*     (2006.01)
    *A61B 8/12*     (2006.01)
    *A61B 5/00*     (2006.01)
    *A61B 7/00*     (2006.01)
    *A61M 16/00*     (2006.01)
    *A61B 5/091*     (2006.01)

(52) U.S. Cl.
CPC ........ *A61M 16/0003* (2014.02); *A61M 16/04* (2013.01); *A61B 5/6847* (2013.01); *A61B 8/12* (2013.01); *A61B 2562/0204* (2013.01)

(56) References Cited

U.S. PATENT DOCUMENTS

| | | | | |
|---|---|---|---|---|
| 4,981,470 A * | 1/1991 | Bombeck, IV | ........ | A61B 5/037 128/205.23 |
| 5,165,417 A * | 11/1992 | Murphy, Jr. | ........... | A61B 7/003 181/126 |
| 5,477,860 A * | 12/1995 | Essen-Moller | .......... | A61B 5/03 600/529 |
| 5,666,960 A | 9/1997 | Fredberg et al. | | |
| 5,746,699 A | 5/1998 | Fredberg et al. | | |
| 5,810,741 A | 9/1998 | Essen-Moller | | |
| 5,882,314 A | 3/1999 | Fredberg et al. | | |
| 6,159,158 A * | 12/2000 | Lowe | ..................... | A61B 5/036 600/529 |
| 6,164,277 A | 12/2000 | Merideth | | |
| 6,168,568 B1 * | 1/2001 | Gavriely | ................ | A61B 5/087 600/529 |
| 6,261,238 B1 * | 7/2001 | Gavriely | ................ | A61B 5/087 600/532 |
| 6,440,083 B1 | 8/2002 | Fredberg et al. | | |
| 6,443,907 B1 * | 9/2002 | Mansy | ..................... | A61B 7/04 600/529 |
| 6,527,729 B1 | 3/2003 | Turcott | | |
| 7,998,091 B2 | 8/2011 | Carim et al. | | |
| 8,333,718 B2 | 12/2012 | Carim et al. | | |
| 8,394,031 B2 * | 3/2013 | Mansy | .................. | A61B 7/003 600/550 |
| 8,517,016 B2 * | 8/2013 | Caro | ...................... | A61B 5/085 128/200.24 |
| 8,591,429 B2 | 11/2013 | Yang | | |
| 8,652,029 B2 | 2/2014 | Hotto et al. | | |
| 8,784,329 B2 * | 7/2014 | Wilson | .................... | A61B 5/087 600/459 |
| 2003/0018276 A1 * | 1/2003 | Mansy | .................. | A61B 7/003 600/529 |
| 2003/0100843 A1 * | 5/2003 | Hoffman | ............... | A61B 5/0809 600/538 |
| 2006/0149127 A1 | 7/2006 | Seddiqui et al. | | |
| 2006/0243280 A1 * | 11/2006 | Caro | ...................... | A61B 5/085 128/204.23 |
| 2007/0113654 A1 | 5/2007 | Carim et al. | | |
| 2007/0118054 A1 | 5/2007 | Pinhas et al. | | |
| 2007/0225613 A1 | 9/2007 | Mabary et al. | | |
| 2007/0244406 A1 * | 10/2007 | Kushnir | ................. | A61B 7/003 600/538 |
| 2008/0275349 A1 | 11/2008 | Halperin et al. | | |
| 2011/0213271 A1 | 9/2011 | Telfort et al. | | |
| 2011/0213272 A1 | 9/2011 | Telfort et al. | | |
| 2011/0213273 A1 | 9/2011 | Telfort et al. | | |
| 2011/0213274 A1 | 9/2011 | Telfort et al. | | |
| 2011/0301414 A1 | 12/2011 | Hotto et al. | | |
| 2011/0301503 A1 | 12/2011 | Carim et al. | | |
| 2012/0123286 A1 * | 5/2012 | Wilson | ................... | A61B 5/087 600/529 |
| 2012/0132211 A1 | 5/2012 | Halperin et al. | | |
| 2012/0203101 A1 | 8/2012 | Prough et al. | | |
| 2013/0289348 A1 | 10/2013 | Hotto et al. | | |
| 2014/0058244 A1 * | 2/2014 | Krocak | ................ | A61B 5/0095 600/407 |
| 2014/0330151 A1 * | 11/2014 | Wilson | ................... | A61B 5/087 600/529 |

\* cited by examiner

DEVICES FOR DIAGNOSING SLEEP APNEA OR OTHER CONDITIONS AND RELATED SYSTEMS AND METHODS

CROSS-REFERENCE TO RELATED APPLICATIONS AND PRIORITY CLAIM

This application is a continuation of U.S. patent application Ser. No. 14/336,185 filed on Jul. 21, 2014, which is a continuation of U.S. patent application Ser. No. 13/167,165 filed on Jun. 23, 2011 (now U.S. Pat. No. 8,784,329), which claims the benefit of U.S. Provisional Application No. 61/413,736 filed on Nov. 15, 2010. All of these patent applications are hereby incorporated by reference in their entirety.

TECHNICAL FIELD

This disclosure is generally directed to medical devices and related treatments. More specifically, this disclosure relates to devices for diagnosing sleep apnea or other conditions and related systems and methods.

BACKGROUND

Obstructive sleep apnea (OSA) is a condition that affects tens of millions of people in the United States and around the world. Obstructive sleep apnea typically occurs when a person's muscles relax during sleep, allowing soft tissue to obstruct the person's upper airway. As a result, the person is asleep but unable to breathe. This often causes the person to partially or completely awaken, at which point the person begins breathing normally and falls back asleep. The process can then repeat itself, possibly multiple times per hour. This condition interferes with the person's sleep patterns and can lead to a whole host of medical problems.

One conventional approach for identifying obstructive sleep apnea involves polysomnography, also known as a sleep study. Unfortunately, polysomnography is typically expensive, time consuming, and cumbersome to perform, so compliance and follow-through are often low. Another conventional approach for identifying obstructive sleep apnea involves home monitoring. However, this approach therefore uses indirect measurements of characteristics such as oxygen saturation and externally-monitored snoring, so it often has low specificity.

SUMMARY

This disclosure provides devices for diagnosing sleep apnea or other conditions and related systems and methods.

In a first embodiment, an apparatus includes a body configured to be inserted into an airway of a patient. The apparatus also includes one or more sensors mounted in or on the body. The one or more sensors are configured to collect sensor data associated with the airway of the patient.

In a second embodiment, a system includes a sensor device having a body configured to be inserted into an airway of a patient and one or more sensors mounted in or on the body. The one or more sensors are configured to collect sensor data associated with the airway of the patient. The system also includes a signal analyzer configured to analyze the sensor data.

In a third embodiment, a computer readable medium embodies a computer program. The computer program includes computer readable program code for receiving sensor data from a sensor device that is configured to be inserted into an airway of a patient. The data is associated with the airway of the patient. The computer program also includes computer readable program code for analyzing the sensor data to determine if the patient suffers from a specified condition affecting the airway of the patient.

In a fourth embodiment, a method includes placing a patient under sedation and inserting a sensor device into an airway of the patient. The method also includes collecting sensor data associated with the patient using the sensor device and analyzing the sensor data to determine if the patient suffers from a specified condition affecting the airway of the patient.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

FIG. 1 through 7, described below, and the various embodiments used to describe the principles of the present invention in this patent document are by way of illustration only and should not be construed in any way to limit the scope of the invention. Those skilled in the art will understand that the principles of the present invention may be implemented in any type of suitably arranged device or system.

Figure 1:
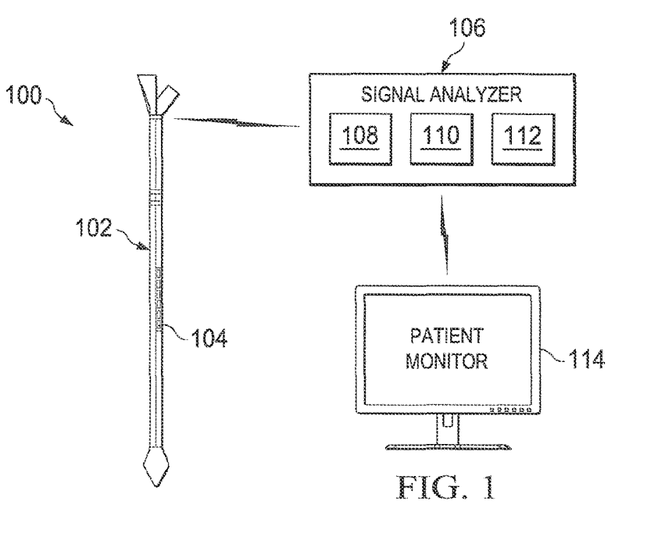
FIG. 1 illustrates an example system for diagnosing sleep apnea or other conditions in accordance with this disclosure.

FIG. 1 illustrates an example system 100 for diagnosing sleep apnea or other conditions in accordance with this disclosure. In this example, the system 100 includes a sensor device 102 that can be inserted into the upper airway of a patient. For example, the sensor device 102 could be inserted through the mouth or nose of the patient into the patient's upper airway. The sensor device 102 includes one or more sensors 104 for measuring one or more characteristics of the patient.

Any suitable type(s) of sensors 104 could be used in the sensor device 102, such as specialized acoustic devices. Also, the sensors 104 could measure any suitable characteristic(s) of the patient. The sensors 104 could, for example, measure the loudness/volume, pitch, or acoustic resonance of vibrations or other noise in the patient's airway. Other measurements that could be taken by the sensors 104 include respiratory effort, blood oxygen level, heart rate, airway temperature variations, and/or airway pressure or manometry. Any other or additional sensor measurements could also be taken and used in the system 100.

The sensor device 102 communicates with a signal analyzer 106. The signal analyzer 106 performs one or more signal analysis functions to analyze the data from the sensor device 102. For example, the signal analyzer 106 could identify the location(s) of sounds produced within the patient's airway. This could be accomplished, for instance, by analyzing a series of sensor measurements taken in sequence along the sensor device 102. The signal analyzer 106 could also analyze the volume, pitch, location, or other information from the sensor device 102 in order to determine the likelihood that the patient suffers from obstructive sleep apnea or other condition(s). This could include the signal analyzer 106 performing pattern recognition to identify whether one or more patterns of airway noise are present in the patient's airway.

The signal analyzer 106 could perform a wide variety of functions to support the analysis of the data from the sensor device 102. These functions could include signal amplification, filtering, noise suppression, pattern detection, and/or FFT, wavelet, or other frequency domain decomposition. The exact signal processing to be performed can vary depending on various factors, such as the condition(s) to be detected and the type(s) of data being analyzed.

The signal analyzer 106 could be implemented in any suitable manner. For example, the signal analyzer 106 could include at least one processing unit 108 that analyzes the sensor data. The processing unit 108 could include a microprocessor, microcontroller, digital signal processor (DSP), field programmable gate array (FPGA), application specific integrated circuit (ASIC), or other processing device. The signal analyzer 106 could also include at least one memory unit 110 that stores instructions and data used, generated, or collected by the processing unit 108. The memory unit 110 could include any suitable volatile and/or non-volatile storage and retrieval device(s). In addition, the signal analyzer 106 could include at least one interface 112 for transmitting data to or receiving data from external devices or systems (such as the sensor device 102). The interface 112 could represent any suitable wired or wireless interface(s), such as a wired serial interface or a wireless radio frequency (RF) transceiver. The signal analyzer 106 could be implemented using only hardware circuits, or the signal analyzer 106 could be implemented using software/firmware instructions executed by a suitable processing device.

The signal analyzer 106 could optionally receive data from at least one patient monitor 114. The patient monitor 114 could monitor one or more additional characteristics of the patient. For example, the patient monitor 114 could monitor the patient's blood pressure, blood oxygen content, depth of sedation, or any other suitable characteristic(s) of the patient.

A single sensor 104 or multiple sensors 104 could be used in the sensor device 102. If multiple sensors 104 are used, the sensors 104 could be read in sequence in order to help identify the location of vibrations or other characteristic(s) within the patient's airway. The signal analyzer 106 could then perform operations to, for example, detect the areas of greatest obstruction by identifying patterns of noise that correspond to clinically important sleep apnea or other conditions. This allows for the detection of patterns in the vibrations or other noise within the patient's airway, which could make evaluation more useful than conventional approaches.

Additional details regarding the sensor device 102 and the signal analyzer 106 are provided below. Also, additional details regarding the use of the sensor device 102 and the signal analyzer 106 are provided below.

Although FIG. 1 illustrates one example of a system 100 for diagnosing sleep apnea or other conditions, various changes may be made to FIG. 1. For example, the sensor device 102 could have any suitable size or shape and include any suitable number of sensors 104. Also, the functional division shown in FIG. 1 is for illustration only. Various components in FIG. 1 could be combined, further subdivided, or omitted and additional components could be added according to particular needs.

Figure 2:
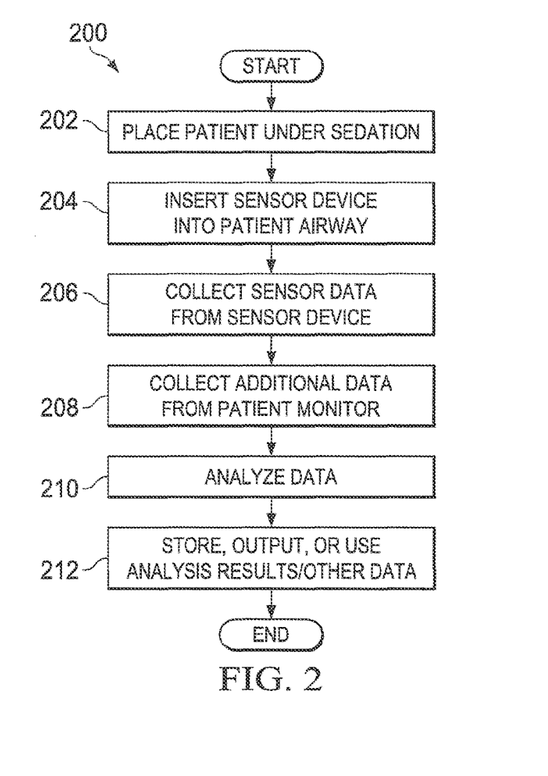
FIG. 2 illustrates an example method for diagnosing sleep apnea or other conditions in accordance with this disclosure.

FIG. 2 illustrates an example method 200 for diagnosing sleep apnea or other conditions in accordance with this disclosure. For ease of explanation, the method 200 is described with respect to the system 100 of FIG. 1. The method 200 could be used with any other suitable sensor device or system.

In this example, a patient is placed under sedation at step 202. The sedation here could involve moderate sedation or some other level of sedation that approximates the conditions of normal sleep. In some embodiments, moderate sedation can be safely performed in a monitored outpatient setting, such as in ambulatory or other surgical centers or sleep centers licensed for sedation, using drugs such as Propofol or Versed. The level of sedation can also be carefully monitored and titrated in a specified range, such as by using a bispectral index (BIS) monitor. A BIS reading between 70 and 80 might be used during the method 200.

Figure 3:
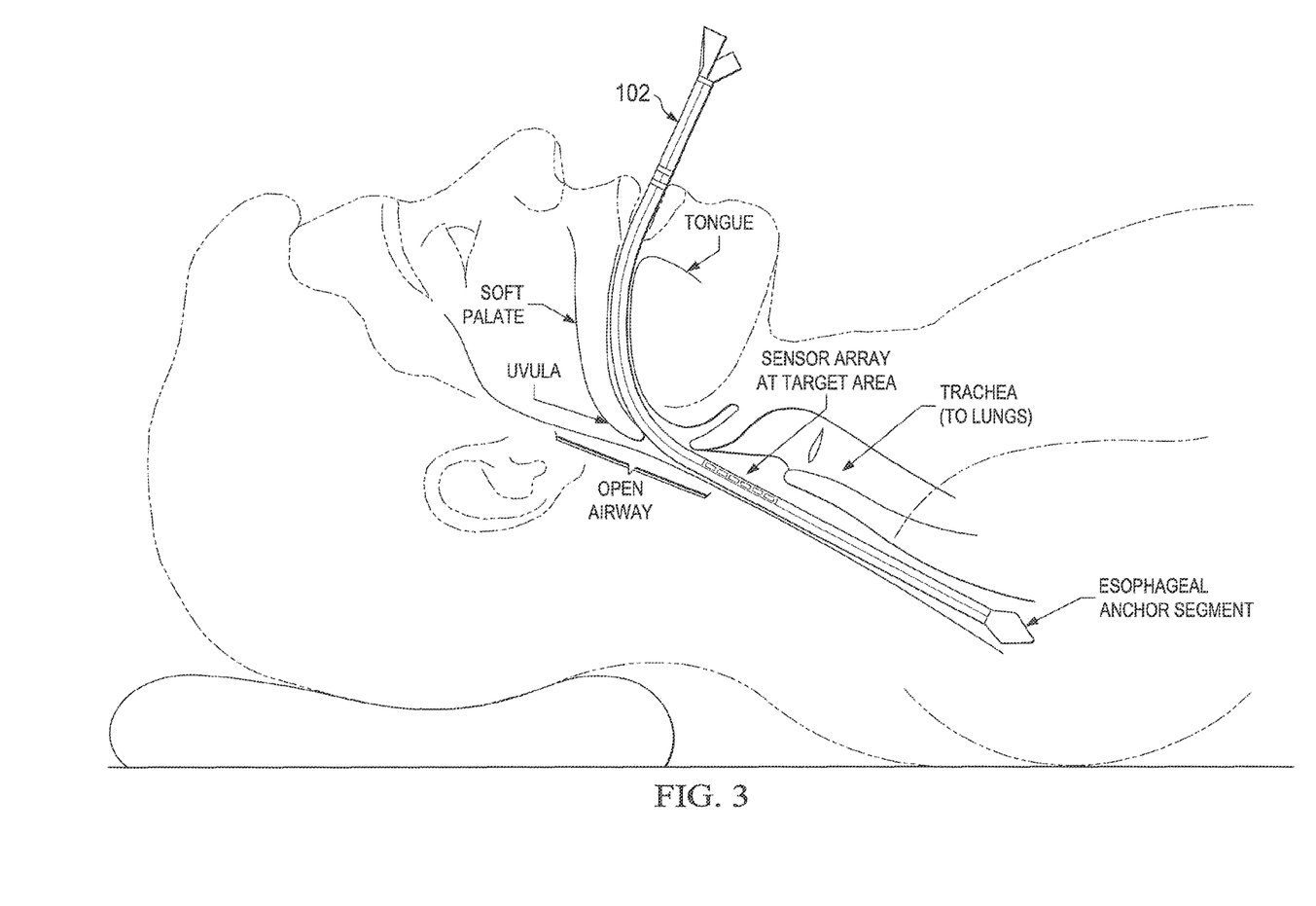
FIGS. 3 and 4 illustrate examples of insertion of a sensor device into a patient's airway in accordance with this disclosure.
Figure 4:
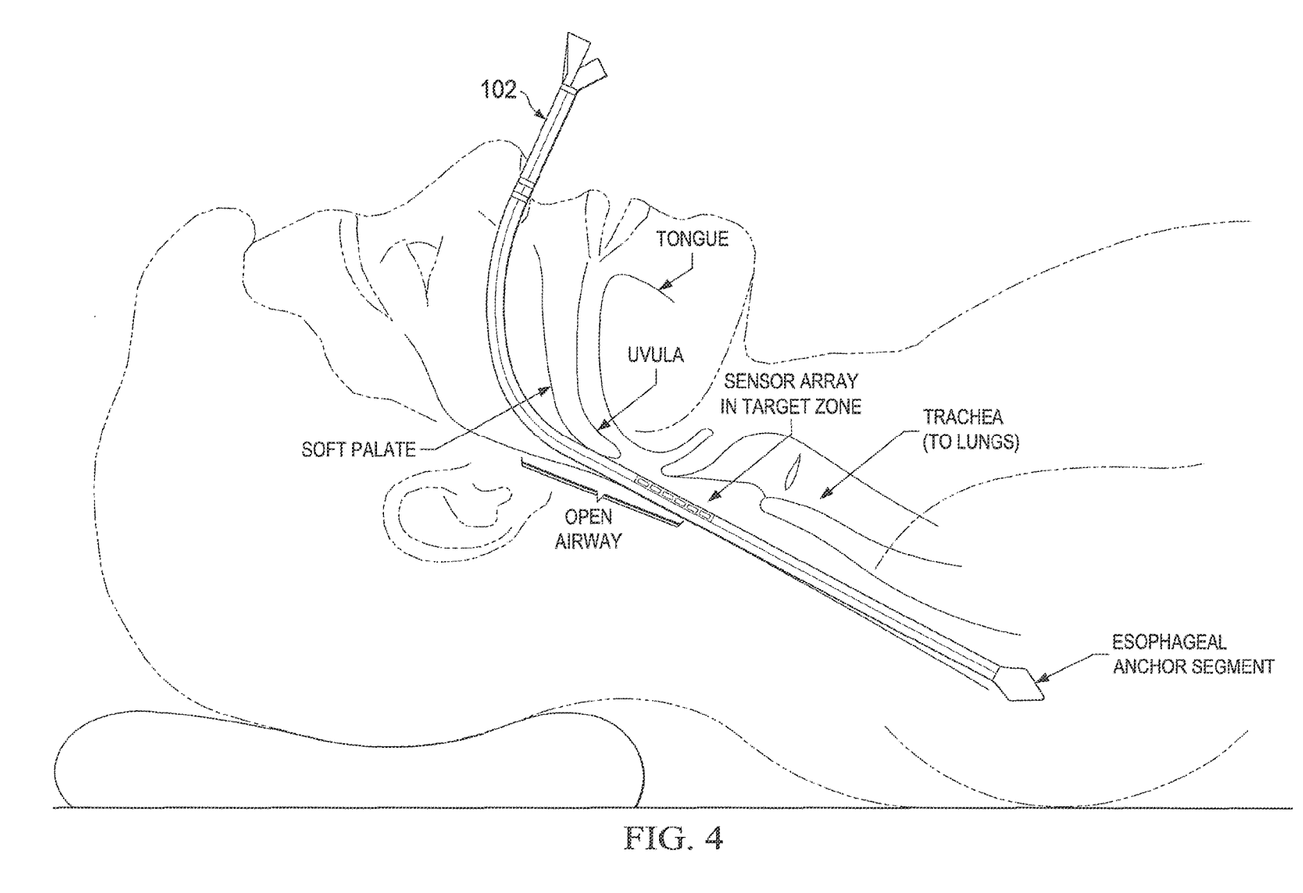

A sensor device is inserted into the patient's airway at step 204. This could include, for example, inserting the sensor device 102 into the patient's upper airway through the patient's mouth or nose. FIGS. 3 and 4 illustrate examples of insertion of the sensor device 102 into a patient's airway in accordance with this disclosure. The sensor device 102 can be inserted through the patient's mouth (FIG. 3) or nose (FIG. 4). Depending on the implementation, different catheters could be used for different insertion paths (such as esophageal and nasal catheters), or the same catheter could be used for either insertion route. The distance of insertion would differ depending on the insertion route, where the nasal route requires further insertion. Markings on a catheter could be created for one or both insertion routes, such as to mark when the sensors 104 have likely be placed into appropriate positions within the patient's upper airway. The most distal sensor 104 in the device 102 could be positioned into or near the patient's cricopharyngeal area.

Sensor data is collected from the sensor device at step 206, and additional data can optionally be collected from a patient monitor (such as the patient monitor 114) at step 208. The data collected could include loudness/volume, pitch, or acoustic resonance of vibrations or other noise in the patient's airway. The data could also include respiratory effort, airway temperature variations, and/or airway pressure or manometry. The data could further include the patient's blood pressure, blood oxygen level, heart rate, depth of sedation, or any other suitable characteristic(s) of the patient.

The data is analyzed at step 210. This could include, for example, the signal analyzer 106 determining the likelihood that the patient is suffering from obstructive sleep apnea or other condition(s) using the collected data. The analysis could involve identification of noise measurements in sequence along the sensor device 102, which supports detection of patterns or anatomic locations of the noise. As a particular example, the signal analyzer 106 could receive a separate noise or other input signal from each microphone or other sensor 104 and analyze the signals together. Among other things, this allows for pattern detection and interpretation by an analysis algorithm. Noise volume, pitch, and pattern could be an indication of airflow turbulence and a degree of upper airway obstruction.

The analysis results and optionally other data are stored, output, or used in some manner at step 212. This could include, for example, the signal analyzer 106 displaying the analysis results for review by medical personnel, storing the analysis results for later use, or using the analysis results to identify or recommend possible treatment options.

In the method 200, the use of a suitable level of sedation can help to imitate the effects of sleep in a patient. For example, snoring is audible airway noise caused by airflow interruptions in the upper airway during sleep. Sedation also produces snoring by the same mechanism. Because the sensor device 102 can be placed directly into the affected area, the sensor device 102 could be much more sensitive in determining airway obstructions and would be able to measure airflow turbulence and partial obstructions before audible snoring is produced.

Moreover, patients often describe difficulties sleeping in monitored settings, and traditional sleep studies often require all night monitoring. With the rise of obesity and sleep apnea, a better and more convenient method of predicting airflow obstruction is needed. The sensor device 102 here can be inserted during carefully monitored sedation, and the patient would not be required to achieve a sleeping state. In fact, this technique can be performed in an outpatient setting or even at home under supervision. As a result, the patient may not be required to undergo inconvenient sleep studies, and results can be obtained more quickly and easily. In addition, the level of sedation can be carefully monitored during this procedure to achieve reproducible and reliable results.

Although FIG. 2 illustrates one example of a method 200 for diagnosing sleep apnea or other conditions, various changes may be made to FIG. 2. For example, various steps in FIG. 2 could overlap, occur in parallel, occur in a different order, or occur multiple times. While FIGS. 3 and 4 illustrate examples of the insertion of the sensor device 102 into a patient's airway, any other suitable technique could be used to place the sensor device 102 in a suitable location within the patient's airway.

Figure 5A:
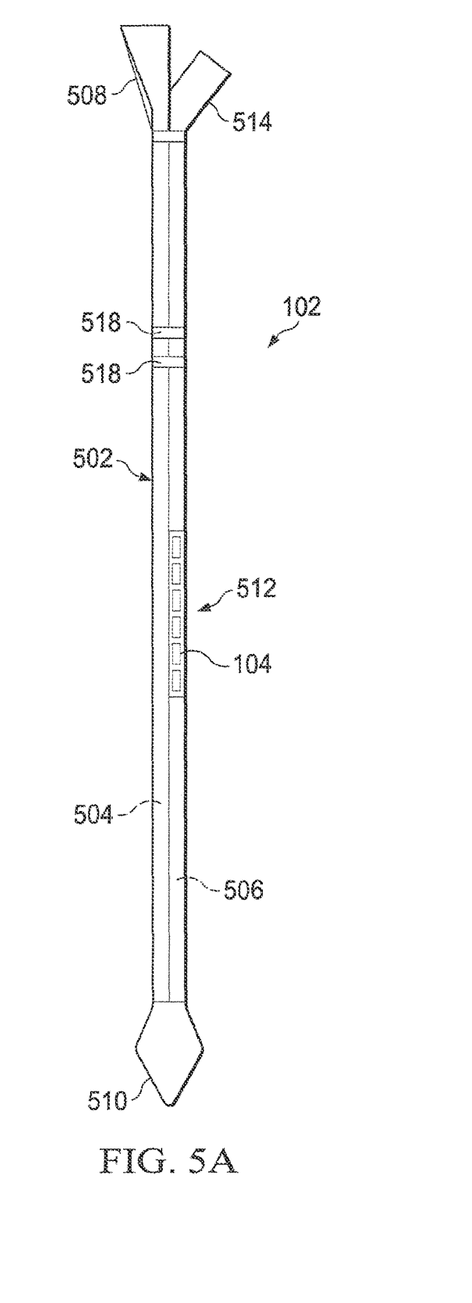
FIGS. 5A and 5B illustrate an example sensor device for diagnosing sleep apnea or other conditions in accordance with this disclosure.
Figure 5B:
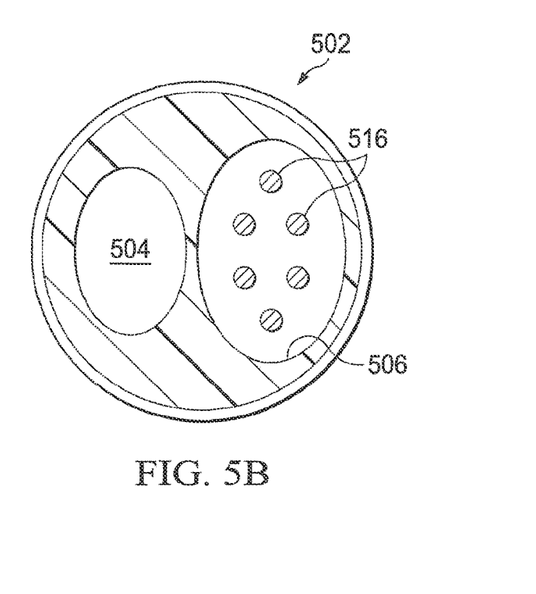

FIGS. 5A and 5B illustrate an example sensor device 102 for diagnosing sleep apnea or other conditions in accordance with this disclosure. As shown in FIG. 5A, the sensor device 102 includes an elongated body 502 having different channels 504-506. In this example, a stylet access channel 504 runs the length of the sensor device 102 from a stylet access port 508 to a tip 510. The stylet access channel 504 can receive a stylet, such as a braded stainless steel wire stylet, which provides stiffness during insertion of the sensor device 102 into a patient's airway. When the stylet is removed, the body 502 could be very soft and flexible, thus creating little interference to any obstructions being measured within the patient's airway.

An electronics access channel 506 allows wires from sensors 104 in a sensor array 512 to be coupled to an electronics access port 514. FIG. 5B illustrates the wires 516 in the electronics access channel 506, as well as the stylet access channel 504 within the body 502. An external device or system could be physically coupled to the electronics access port 514 in order to communicate with the sensor array 512, or a wired or wireless transceiver could allow remote devices or systems to engage in wired or wireless communications with the sensor array 512.

One or more markings 518 can be used to identify the desired insertion distance for one or more insertion routes. In many patients, there could be about 10 cm between the patient's incisors and uvula and about 14 cm between the patient's incisors and the top of the trachea. There could also be about 12 cm between the patient's nostrils and uvula and about 16 cm between the patient's nostrils and the top of the trachea. These distances may be accurate to within ±10% for most patients, so the markings 518 can be used to identify the correct insertion distances for the oral and nasal insertions.

The body 502 includes any suitable structure for insertion into a patient's airway, such as a pharyngometer catheter. As a particular example, the body 502 could represent a catheter having a 12 French catheter size (a diameter of 3 mm to 4 mm), although the actual diameter may depend on the type(s) of instrument(s) inside the catheter and the number of wires needed. The body 502 could be formed from any suitable material(s), such as a soft flexible polyurethane like Teclthane polyurethane. The total length of the body 502 could be about 50 cm. Extra length at the end of the body 502 (opposite the ports 508 and 514) can provide for an esophageal anchor segment that supports stable position and safe insertion. The body 502 may be long enough to reach the mid-esophagus and allow for safe insertion while keeping the sensor array 512 in the proper location to detect airway noise.

The access channels 504-506 include any suitable structures for receiving a stylet and electrical connections, respectively. The stylet access channel 504 could have a length of about 48 cm. The electronics access channel 506 could have a length of about 32 cm from the port 514 to the sensor array 512 and about 38 cm from the port 514 to the last sensor 104 in the array 512.

The marking(s) 518 could identify any suitable location(s) on the sensor device 102. For example, the distance between the top of the sensor device 102 and the nasal marking could be about 20 cm, and the distance between the top of the sensor device 102 and the oral marking could be about 22 cm. There could be about 10 cm between the oral marking and the first sensor 104 in the sensor array 512 and about 16 cm between the oral marking and the last sensor 104 in the sensor array 512.

The sensor array 512 includes any suitable structure having any number of sensors 104, such as a closed sensor array containing digital output sensors. The length of the sensor array 512 could be about 6 cm to allow coverage over at least 4 cm of the patient's airway regardless of the insertion route. However, smaller or larger arrays could also be used, such as an array spanning about 4 cm from about 11 cm to about 15 cm from the oral insertion marking. Any number of sensors 104 could be used in the sensor array 512, such as four to six sensors.

Any type(s) of sensor(s) 104 could be used in the sensor array 512. For example, the sensors 104 could include an array of microphone chips, such as those available for use in mobile telephones, laptop computers, or BLUETOOTH devices. Omni-directional or uni-directional digital output microphones or other microphones may be used to reduce interference and increase positional awareness. Beam-steering and noise-cancellation technology can be used to maximize the effectiveness of measurements inside the airway. The microphones may or may not be evenly spaced within the sensor array 512. The sensors 104 could also be sealed within a thin water-proof package to provide protection from moisture in the patient's airway while also allowing for easy catheter construction. In particular embodiments, monolithic CMOS MEMS microphone chips or similar chips could be used as the sensors 104. The approximate size of the microphone chips could be about 1 mm to about 2 mm in length (although other sizes could be used), and the chips could generate outputs over thin wires or other wired/wireless connections. Note that multiple microphones could be used within the sensor array 512 to measure one or multiple characteristics associated with the patient.

The stylet access port 508 includes any suitable structure for providing access to the stylet access channel 504. The electronics access port 514 includes any suitable structure for providing access to the electronics access channel 506. The wires 516 include any suitable conductive structures for carrying electrical signals. Note, however, that the sensor array 512 could incorporate wireless technology, which could reduce or eliminate the number of wires 516 in the electronics access channel 506. In this case, the electronics access channel 506 could simply hold the sensor array 512. The tip 510 includes any suitable structure terminating the body 502, such as a pliable weighted solid tip at the end of an esophageal anchor segment. As a particular example, the tip 510 could represent a pliable heavy rubber core with a polyurethane outer shell. The tip 510 could have a length of about 2 cm.

Although FIGS. 5A and 5B illustrate one example of an embodiment of the sensor device 102, various changes may be made to FIGS. 5A and 5B. For example, the shapes, relative sizes, and dimensions of various structures in the sensor device 102 are for illustration only. Other sensor devices having differing components could be used, such as those in which the body 502 has a different shape or a different cross-section.

Figure 6:
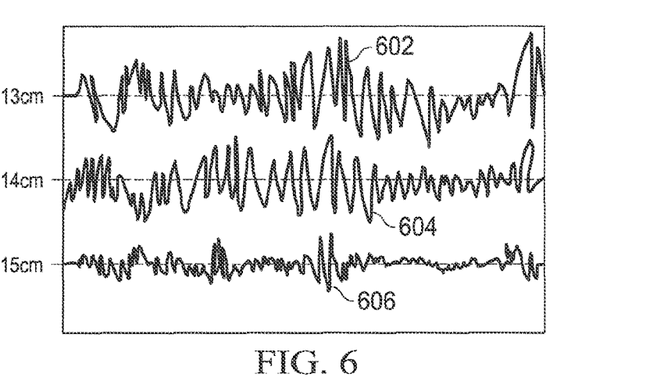
FIGS. 6 and 7 illustrate details of an example analysis of signals by a signal analyzer in accordance with this disclosure.

FIGS. 6 and 7 illustrate details of an example analysis of signals by the signal analyzer 106 in accordance with this disclosure. As shown in FIG. 6, the signal analyzer 106 can receive multiple signals, such as signals 602-606, from the sensor device 102. In this example, the signals 602-606 are generated by different sensors 104 located at different distances within the patient's airway (larger distances indicating farther insertion into the airway). The signals 602-606 could represent any suitable information, such as volume, pitch, or resonance of vibrations or other noise in the patient's airway. The signals 602-606 can be analyzed by the signal analyzer 106 in any suitable manner.

Figure 7:
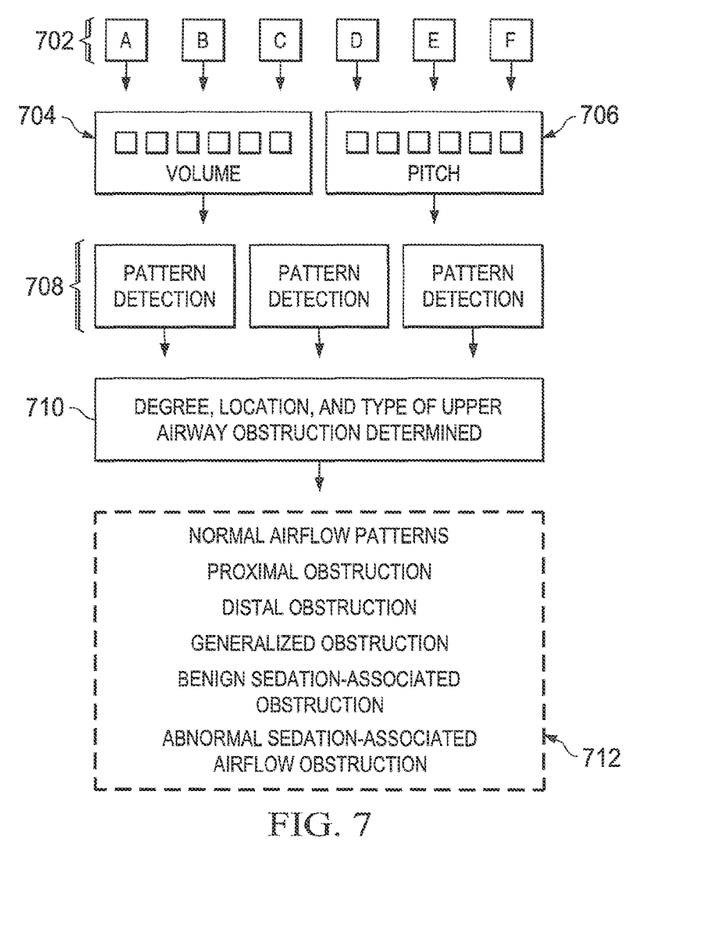

One example analysis technique is shown in FIG. 7. In this example, the sensors 104 can output signals 702 to the signal analyzer 106, such as in sequence based on the order of the sensors 104 within the sensor array 512. The sequences can be analyzed by the signal analyzer 106 to determine various sound characteristics of the signals 702, such as volume characteristics 704 and pitch characteristics 706 of the signals 702. The signal analyzer 106 could then perform pattern recognition to identify one or more patterns 708 in the signals 702. The patterns 708 can be associated with different airway obstructions. Specific patterns and their volume, pitch, or other characteristics can be determined experimentally using patients with known types of obstructions. The signal analyzer 106 can use any identified patterns to make an identification 710 of any obstructions detected in the patient's airway. The identification 710 can include a type of obstruction detected, a location of the detected obstruction, and a degree or severity of the detected obstruction. One or more indicators 712 for any identified obstruction(s) could then be stored, output, or otherwise used.

The patterns 706 can be those associated with different obstructions of the airway, such as proximal/middle/distal pharyngeal obstruction, generalized pharyngeal obstruction, or high-pitched proximal/middle/distal pharyngeal obstruction. These obstructions may typically be associated with different patterns of volume and/or pitch measurements, and the signal analyzer 106 can detect and categorize the patterns for interpretation or diagnosis. Note that these obstructions are for illustration only and that any noise patterns or other characteristic(s) indicative of airflow turbulence or tissue interference in airflow could be identified and used.

In this way, the signal analyzer 106 can analyze data captured by the sensor device 102 and determine whether the patient appears to suffer from some type of sleep-related airway obstruction. Note, however, that the sensor device 102 need not be used in conjunction with an analyzer that automatically determines whether a patient appears to suffer from a sleep-related airway obstruction. In other embodiments, for example, the signal analyzer 106 could simply store or output the received signals from the sensor device 102, such as to allow a doctor or other personnel or an external system to analyze the signals.

Although FIGS. 6 and 7 illustrate details of one example analysis of signals by the signal analyzer 106, various changes may be made to FIGS. 6 and 7. For example, the signal analyzer 106 could receive signals from any number of sensors 104 in a sensor device 102. Also, the signal analyzer 106 could perform any other suitable analysis to identify airway obstructions in a patient.

Note that while described above as being used to detect obstructive sleep apnea, measuring sedation-related airflow obstructions may have other useful clinical applications. As a result, the sensor device 102 and/or the signal analyzer 106 could be used for a wide range of other purposes. For example, the sensor device 102 (with or without the signal analyzer 106) could be used to capture Sedation Associated Airway Noise (SAAN) measurements, Sedation Associated Airway Vibration (SAAV) measurements, Sedation Associated Airway Acoustic Resonance/Pitch (SAAR/SAAP) measurements, or Sedation Associated Airway Manometry (SAAM) measurements. The sensor device 102 (with or without the signal analyzer 106) could be used during anesthesia or sedation research, in anesthesia equipment to directly monitor patients during sedation for safety and airway patency, or for otolaryngology surgical research and surgical evaluations. The sensor device 102 (with or without the signal analyzer 106) could be used to determine the best candidates for surgical correction of obstructive sleep apnea, to evaluate the effectiveness of surgery for obstructive sleep apnea, and to evaluate patients with neck or facial trauma for airway patency. The sensor device 102 (with or without the signal analyzer 106) could be used for dental research to determine the effectiveness of and identify the best candidates for obstructive sleep apnea appliances, during clinical research into sleep apnea, and during pharmacological research (such as to determine the effect of certain medications on airway function or snoring). This represents example applications in which the sensor device 102 and possibly the signal analyzer 106 could be used.

Among other things, the devices, systems, and method described in this patent document allow medical personnel to directly and accurately diagnose airflow problems during sedation. This could be done during a stand-alone procedure or as an "add-on procedure" during another procedure that requires sedation, such as a screening colonoscopy. A direct measurement of airway patency may be a better or optimal way to diagnose conditions such as obstructive sleep apnea.

In some embodiments, one or more of the functions described above (such as functions of the signal analyzer 106) are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A system comprising:
a sensor device configured to be inserted through a mouth or a nose of a patient into an upper airway of the patient, the sensor device comprising multiple sensors configured to capture and transmit sensor data at multiple spaced-apart locations along the upper airway of the patient, the sensor data comprising vibrational or acoustic data associated with the upper airway of the patient;
at least one interface configured to receive the sensor data; and
at least one processing device configured to analyze the sensor data to identify one or more obstructions within the upper airway of the patient, wherein the at least one processing device is configured to identify the one or more obstructions within the upper airway of the patient by determining whether one or more patterns of airway noise are present in the upper airway of the patient based on the vibrational or acoustic data captured at the multiple spaced-apart locations along the upper airway of the patient.

2. The system of claim 1, wherein the at least one interface is physically coupled to the sensor device.

3. The system of claim 1, wherein the at least one processing device is configured to identify at least one of: volume characteristics and pitch characteristics of the sensor data.

4. The system of claim 3, wherein the at least one processing device is configured to perform pattern recognition in order to identify the one or more patterns using at least one of the volume characteristics and the pitch characteristics of the sensor data.

5. The system of claim 4, wherein the at least one processing device is configured to use the one or more patterns to identify at least one of: a type, a location, and a degree of the one or more obstructions within the upper airway of the patient.

6. The system of claim 1, wherein the at least one processing device is configured to identify one or more locations of one or more sounds within the upper airway of the patient using the sensor data.

7. The system of claim 1, wherein the at least one processing device is configured to identify one or more areas of greatest obstruction within the upper airway of the patient using the sensor data.

8. The system of claim 1, wherein the at least one processing device is configured to analyze the sensor data to determine if the patient suffers from obstructive sleep apnea.

9. The apparatus of claim 1, wherein the sensor data further comprises airway pressure within the upper airway of the patient.

10. A method comprising:
capturing sensor data comprising vibrational or acoustic data using a sensor device, the sensor device configured to be inserted through a mouth or a nose of a patient into an upper airway of the patient, the sensor device comprising multiple sensors configured to capture the vibrational or acoustic data associated with the upper airway of the patient at multiple spaced-apart locations along the upper airway of the patient; and
analyzing the sensor data to identify one or more obstructions within the upper airway of the patient, wherein analyzing the sensor data comprises determining whether one or more patterns of airway noise are present in the upper airway of the patient based on the vibrational or acoustic data captured at the multiple spaced-apart locations along the upper airway of the patient.

11. The method of claim 10, wherein the one or more patterns comprise at least one of:
proximal, middle, or distal pharyngeal obstruction;
generalized pharyngeal obstruction; and
high-pitched proximal, middle, or distal pharyngeal obstruction.

12. The method of claim 10, wherein analyzing the sensor data comprises identifying at least one of: volume characteristics and pitch characteristics of the sensor data.

13. The method of claim 12, wherein analyzing the sensor data comprises performing pattern recognition in order to identify the one or more patterns using at least one of the volume characteristics and the pitch characteristics of the sensor data.

14. The method of claim 13, wherein analyzing the sensor data comprises using the one or more patterns to identify at least one of: a type, a location, and a degree of the one or more obstructions within the upper airway of the patient.

15. The method of claim 10, wherein analyzing the sensor data comprises identifying one or more locations of one or more sounds within the upper airway of the patient using the sensor data.

16. The method of claim 10, wherein analyzing the sensor data comprises identifying one or more areas of greatest obstruction within the upper airway of the patient using the sensor data.

17. The method of claim 10, wherein analyzing the sensor data comprises determining if the patient suffers from obstructive sleep apnea.

18. A system comprising:
a sensor device configured to be inserted through a mouth or a nose of a patient into an upper airway of the patient, the sensor device comprising multiple sensors configured to capture and transmit sensor data at multiple spaced-apart locations along the upper airway of the patient, the sensor data comprising vibrational or acoustic data associated with the upper airway of the patient;

interface circuitry configured to receive the sensor data; and analysis circuitry configured to analyze the sensor data to identify one or more obstructions within the upper airway of the patient, wherein the analysis circuitry is configured to identify the one or more obstructions within the upper airway of the patient by determining whether one or more patterns of airway noise are present in the upper airway of the patient based on the vibrational or acoustic data captured at the multiple spaced-apart locations along the upper airway of the patient.

19. The system of claim 18, wherein the interface circuitry is physically coupled to the sensor device.

20. The system of claim 18, wherein the analysis circuitry is configured to:

identify at least one of: volume characteristics and pitch characteristics of the sensor data;

perform pattern recognition in order to identify the one or more patterns using at least one of the volume characteristics and the pitch characteristics of the sensor data; and use the one or more patterns to identify at least one of: a type, a location, and a degree of the one or more obstructions within the upper airway of the patient.

21. The system of claim 18, wherein the analysis circuitry is configured to at least one of:

identify one or more locations of one or more sounds within the upper airway of the patient using the sensor data; and identify one or more areas of greatest obstruction within the upper airway of the patient using the sensor data.

* * * * *